United States Patent [19]

Talish et al.

[11] Patent Number: 5,211,160

[45] Date of Patent: May 18, 1993

[54] ULTRASONIC ORTHOPEDIC TREATMENT HEAD AND BODY-MOUNTING MEANS THEREFOR

[75] Inventors: Roger J. Talish, Fairfield; Arthur L. Lifshey, East Brunswick, both of N.J.

[73] Assignee: Interpore Orthopaedics, Inc., West Caldwell, N.J.

[21] Appl. No.: 671,350

[22] Filed: Mar. 19, 1991

Related U.S. Application Data

[63] Continuation-in-part of Ser. No. 628,403, Dec. 17, 1990, which is a continuation-in-part of Ser. No. 247,105, Sep. 14, 1988, Pat. No. 5,003,695.

[51] Int. Cl.$^5$ ............................................. A61B 17/56
[52] U.S. Cl. ............................ 128/24 AA; 128/419 F
[58] Field of Search ............. 128/419 F, 804, 24 AA, 128/802

[56] References Cited

U.S. PATENT DOCUMENTS

| | | | |
|---|---|---|---|
| 4,266,533 | 5/1981 | Ryaby et al. | 128/419 F |
| 4,501,265 | 2/1985 | Pescatore | 128/419 F |
| 4,556,051 | 12/1985 | Maurer | 128/419 F |
| 4,574,809 | 3/1986 | Talish et al. | 128/419 F |
| 4,757,804 | 7/1988 | Griffith et al. | 128/419 F |

*Primary Examiner*—Ruth S. Smith
*Attorney, Agent, or Firm*—Hopgood, Calimafde, Kalil, Blaustein & Judlowe

[57] ABSTRACT

The invention contemplates an improved strap or bandage mounting of a socket element for removably engaged coupling of an ultrasonic transducer element to an afflicted limb. In a preferred embodiment, a radially flanged annular socket element is formed with outward lugs at axial offset from the flange, for preliminary assembly to a length of bandage material which has been cut to provide an opening for registration with the bore of the socket element, with the flange surrounding the opening and against one side of the bandage, while the outward lugs engage the other side of the bandage and also assure the desired registration. A softly compliant pad having a similar opening is removably securable to the flange-mounted side of the bandage to hold registration of the same central opening for all components and to afford direct access to an afflicted body-limb region through the central opening, when the thus-assembled bandage has been wrapped around the limb to securely position the socket element for reception of the transducer of a treatment head. Bayonet-locking lug formations on or near the transducer part of the head coact with lug formations on the socket element to retain the transducer during treatment of an afflicted bone through gel-coupled flesh at the situs of injury.

18 Claims, 3 Drawing Sheets

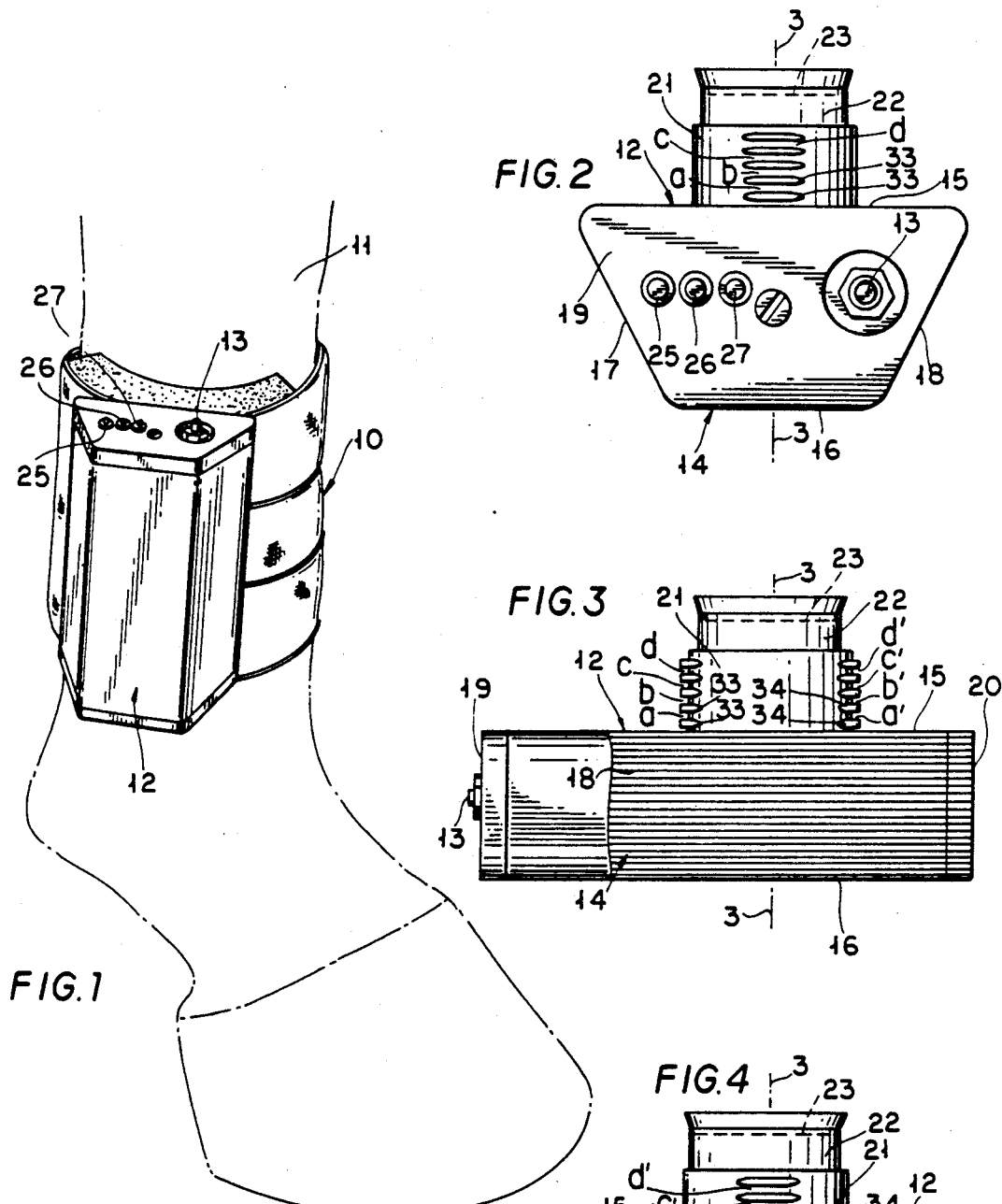
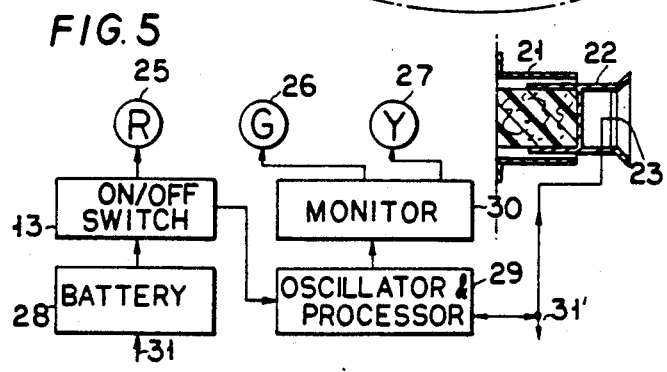

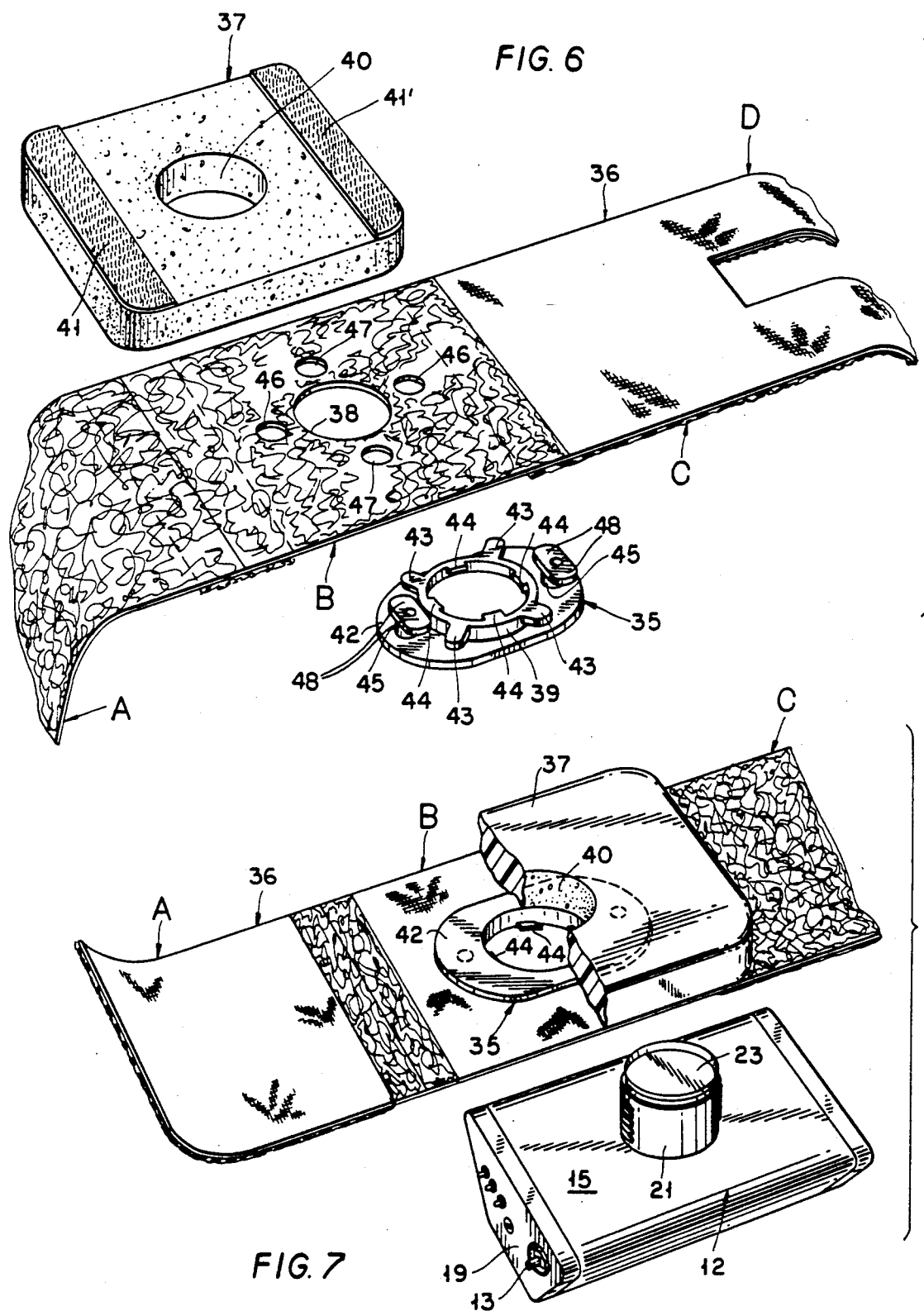

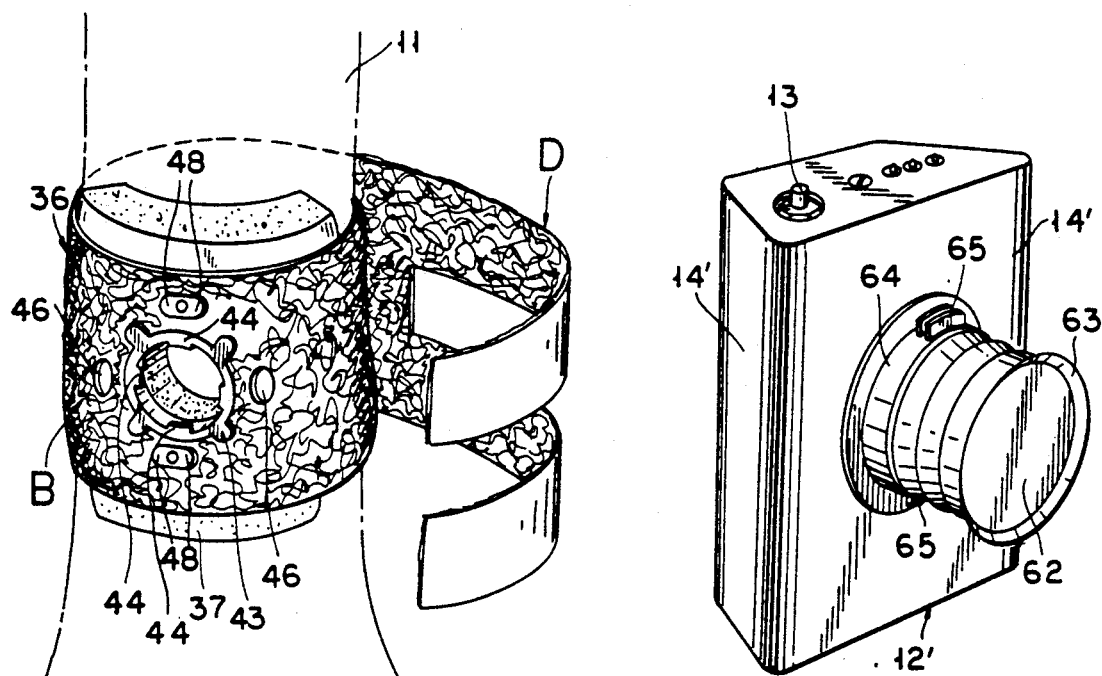
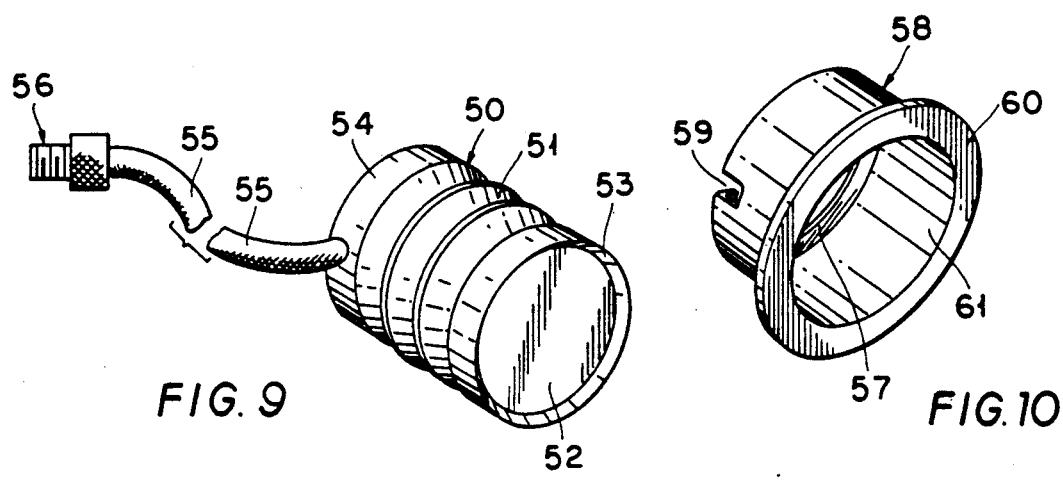

even though the aspect of FIG. 7 is otherwise substantially the same as that of FIG. 6;

ULTRASONIC ORTHOPEDIC TREATMENT HEAD AND BODY-MOUNTING MEANS THEREFOR

RELATED CASES

This application is a continuation-in-part of copending application Ser. No. 628,403, filed Dec. 17, 1990, and said copending application is a continuation-in-part of original application, Ser. No. 247,105, filed Sept. 14, 1988, now U.S. Pat. No. 5,003,695. The disclosures of said applications are hereby incorporated by reference.

BACKGROUND OF THE INVENTION

The invention relates to use of ultrasonic radiation at relatively low levels into living tissue, as for the non-invasive healing treatment of bone fractures, pseudarthroses and the like.

Duarte U.S. Pat. No. 4,530,360 describes a technique of bone defects of the character indicated using a pulsed radio-frequency ultrasonic signal applied via a transducer to the skin of a patient and directed to the site of the defect. The radio-frequency signal is in the range of 1.3 to 2 MHz, and it consists of pulses at a repetition rate of 100 to 1,000 Hz, with each pulse having a duration in the range 10 to 2,000 microseconds. The Duarte apparatus comprises a radio-frequency oscillator connected to a driver, and a pulse generator is arranged to control driver output in accordance with a preselected duration and repetition rate of bursts of radio-frequency oscillations in the driver output. A flexible radio-frequency cable connects driver output to a body applicator, in the form of a hand-held plastic tube, one end of which is closed to mount a piezoelectric transducer, in the form of a thin flat disc, excited for thickness resonance.

Necessarily, therefore, in the Duarte apparatus, the source of electrical energy is remote, as on a table top, and the flexible connection to the body applicator must, in use, always be electrically "live" and, therefore potentially hazardous. Also, for the power levels involved, and considering the fact that two or more transducers seldom can be found to resonate at precisely the same frequency, the radio-frequency must be pretuned to serve one and only one transducer. In other words, apparatus of the Duarte patent necessarily dedicates the remote signal-generating part of the system to the particular applicator. And any attempt to replace a damaged applicator must involve a returning of the signal-generator to the newly substituted applicator. Said application Ser. No. 247,105 is primarily addressed to these problems.

Said application Ser. No. 628,403 is primarily concerned with improved means of flexibly mounting the ultrasonic transducer in apparatus of the character indicated. And the present application addresses various problem aspects of selectively and removably positioning the ultrasonic transducer, particularly in situations wherein, for intervals between therapeutic ultrasonic applications, little or no apparatus, such as a cast, can be tolerated on the body part requiring treatment.

Ultrasonic therapy of the character indicated is found to accelerate natural bone-repair processes of animals, as well as human beings, and the present application particularly address problems of providing such therapy to horses, such as race horses that have sustained bone damage which might otherwise require prolonged side-lining rest and rehabilitation. It is to be understood, however, that much of what is herein described for equine application is also applicable to other animals and to human beings.

BRIEF STATEMENT OF THE INVENTION

It is an object of the invention to provide improved body-applicator apparatus, for use in a ultrasonic device, as of the character disclosed in said copending patent applications.

A specific object is to provide improved means of mounting body-applicator apparatus for ultrasonic treatment of damaged bone tissue, said apparatus being particularly suited for equine use.

Another specific object is to provide a kit of elemental simplicity, for mounting an ultrasonic applicator, to enable fast and effective application to an injured limb of a horse, without materially encumbering the animal or interfering either with its stance or with its walking in the course of recovery from the injury.

The invention meets the above objects by providing, for use in an ultrasonic bone-therapy system of the character indicated, an improved means of bandage or strap-mounting a socket element for removably engaged coupling of an ultrasonic transducer element to an afflicted limb. In a preferred embodiment, a radially flanged annular socket element is formed with outward lugs at axial offset from the flange, for preliminary assembly to a length of bandage material which has been cut to provide an opening for registration with the bore of the socket element, with the flange surrounding the opening and against one side of the bandage, while the outward lugs engage the other side of the bandage and also assure the desired registration. A softly compliant pad having a similar opening is removably securable to the flange-mounted side of the bandage to hold registration of the same central opening for all components and to afford direct access to an afflicted body-limb region through the central opening, when the thus-assembled bandage has been wrapped around the limb to securely position the socket element for reception of the transducer of a treatment head. Bayonet-locking lug formations on or near the transducer part of the head coact with lug formations on the socket element to retain the transducer during treatment of an afflicted bone through gel-coupled flesh at the situs of injury.

DETAILED DESCRIPTION

The invention will be described in detail, in conjunction with the accompanying drawings, in which:

FIG. 1 is a perspective view of an equine leg which, in accordance with the invention, has been adapted to removably mount an ultrasonic-treatment head;

FIG. 2 is a top-plan view of the treatment head of FIG. 1;

FIG. 3 is a fragmentary side elevation of the treatment head of FIG. 1, being as seen upon 90° rotation from FIG. 1 and about the axis 3—3 shown in both FIGS. 2 and 3;

FIG. 4 is a bottom plan view of the treatment head of FIG. 1 being as seen upon 180° rotation from FIG. 2 and about the axis 3—3;

FIG. 5 is a simplified schematic diagram of electronic components of the treatment head of FIG. 1;

FIG. 6 is an exploded view in perspective of separate components of means in FIG. 1 to mount the treatment head of FIGS. 2 to 4;

FIG. 7 is another exploded view in perspective, from an aspect which is the reverse of the aspect in FIG. 6, and showing mounting components in partially assembled relation;

FIG. 8 is a view similar to FIG. 1, to illustrate application of the mounting components of FIGS. 6 and 7 to an equine leg;

FIG. 9 is an isometric view of a transducer-head component, selectively usable with the treatment head of FIGS. 2 to 5;

FIG. 10 is an isometric view of a socket component for mounting the transducer component of FIG. 9; and FIG. 11 is a perspective view of a modified transducer-head unit, usable with the mounting means of FIGS. 1, 6, 7 and 8, instead of the treatment head of FIGS. 2 to 5.

Referring initially to FIG. 1, the invention is shown in application to mounting means in the form of a bandage assembly 10 wrapped around a lower region of an equine leg 11 which has sustained a bone injury such as a fracture, and which is being subjected to ultrasonic therapy, to accelerate normal bone-healing recovery. A treatment-head unit 12 is removably assembled to the bandage assembly 10 and, as will be later explained, is self-contained with its own power supply, oscillator and ultrasonic transducer. The ultrasonic transducer may be a thin flat piezoelectric element, as described in said application Ser. No. 247,105, but it is manually operated for on/off control at 13, as distinguished from the kind of remote control described in Ser. No. 247,105.

FIGS. 2, 3 and 4 show the treatment-head unit 12 to comprise a relatively compact housing 14 of electronic components. The housing is of generally trapezoidal section, with opposing parallel flat front and back surfaces 15, 16, and with side surfaces 17, 18 which diverge in the back-to-front direction. The axis 3—3 is at the lateral center of the front and back surfaces 15, 16 and is preferably located at longitudinal offset from the midpoint of the span between the respective trapezoidal end surfaces 19, 20, as the same is apparent in FIG. 3.

Shown at 21 and centered on axis 3—3 is a rigid tubular projection from the front surface 15 of housing 14. A suitable ultrasonic transducer, such as a thin circular disc 23 is carried at the outer axial end of the tubular projection 21.

The end surface 19 of housing 14 is seen to expose the start/stop button 13 for manual actuation and to provide a display of three indicator lights 25, 26, 27 which provide vital information for proper operation. A red light at 25 indicates that the battery (28) is being charged; a blinking green light at 26 indicates that the device is operating, namely that monitoring circuitry within the housing detects that ultrasonic energy imparted by the transducer is being sufficiently conveyed via the gel and adjacent body tissue, to the intended situs of bone tissue and/or cells; and a yellow light at 27 indicates a low charge of the battery. Monitoring and indicator means of the character indicated are described in greater detail in said application Ser. No. 247,105. It therefore suffices in the simplified schematic diagram of FIG. 5 to show the general connected relationship between these indicator lights 25, 26, 27 and the battery (28), switch (13), oscillator 29, monitor 30, transducer 23, and a battery-charging jack 31. For a purpose which will be explained in connection with FIG. 9, an additional oscillator-output connection 31' is schematically shown in FIG. 5 but is seen in FIG. 4 to provide a jack receptacle for selective delivery of cable-connected excitation for a different transducer, such as the transducer of FIG. 9. When either of the jack receptacles 31, 31' is not in use, a protective flap 32, 32' of elastomer material can be swung about its pivotal connection to the end face 20, and frictionally retained in sealed prospective closure of the jack receptacles 31, 31'.

Description of the body-applicator unit 12 is completed by identifying plural axially spaced sets of lugs or ridges 33, 34 whereby to releasably retain unit 12 in assembled relation to the bandage assembly 10. In FIGS. 2 to 4, one sees that these lugs or ridges 33, 34 are in paired diametrically opposed relation, and that they are integral formations of the projecting fixed cylindrical base of ultimate transducer support, via sleeve 22. Each of these lugs or ridges 33, 34 is of arcuate length which preferably is about 45° about axis 3—3, with tapered limits of arcuate span, for ease of establishing a bayonet-locking mount, involving bandage-assembly lugs in a selected space between axially adjacent lugs or ridges 33, 34. The plural corresponding lugs or ridges 33, 34 thus define a first set a, a' of lug-engageable spaces, a second set b, b' of lug-engageable spaces, and third and fourth sets c, c' and d,d' of lug-engageable spaces, whereby to mount the transducer 23 in optimum proximity to a particular bandage-mounting situation in respect of local body-limb topography.

Reference is now made to FIGS. 6, 7, 8 and 9 for identification of components and features of the bandaging for securely applying a rigid annular socket member 35 to body limb 11. In FIG. 7, the bandaging assembly 10 is seen to comprise three components: an elongate strip 36 of bandaging fabric, a relatively thick pad 37 of softly compliant material such as foamed urethane, and the socket member 35.

The strip 36 of bandaging fabric has four identifiable regions A, B, C, D, and in FIGS. 6 and 7 curls of this fabric will be understood to be suggestive of the ultimately wrapped application of strip 36 to a body limb. Thus, the separate components 35, 36, 37 in FIG. 6 are shown for their outwardly facing aspects, and in FIG. 7, the same components appear for their inwardly facing aspects. Region A of strip 36 is the region which begins a wrap of the involved body limb, and region B is centrally apertured at 38 for accommodation of the axially short, cylindrically tubular body 39 of socket element 35. Region C begins wrapped overlap with region A, depending upon the local circumferential extent of the involved body limb, and region D is an extension of region C, with a central cut-out to define laterally spaced fingers for such wrap of region B as will avoid traversal of the central opening 38. Desirably, hook-and-loop materials, of the commercial variety known by the trademark VELCRO, are so applied to inward and outward surfaces of strip 35 as to assure VELCRO-locked engagement of such wrapped overlaps as apply for involved limbs of different girth. As shown, such materials are applied to the outward surface of regions A and B, and to the inward surface of regions C and D. In addition, it is noted that the inward surface of region B is provided with VELCRO material, at longitudinal limits of region B, for retaining engagement with the resilient pad 37, when its central opening 40 is brought into register with the central opening of region B, it being noted that corresponding longitudinal limits of pad 37 are similarly equipped (at 41, 41') with VELCRO material. However, this latter assembly to strip 36 with pad 37 cannot occur until the socket element 35 has been initially assembled to strip 36.

Socket element 35 is a relatively rigid part which may be a product of injection-molded plastic material. At one axial end of its short tubular body 39, a radial flange 42 of generally oval profile is provided for relatively large-area and circumferentially continuous lap of the inward surface of region B when thus assembled to strip 36, at opening 38. When thus assembled, plural radially outward lugs 43 lap the outward surface of region B, at spaced marginal areas around opening 38. The bore of socket element 35 is seen to include four radially inward bayonet-locking lugs 44 at equal spacings and of such thickness as to have slight interference with a selected one of the spacing sets (a, a', through d, d') of the projecting base 21 of treatment head 12, it being understood that through such an interference-fit relation, any selected axial location of bayonet-locking engagement will be frictionally retained.

To establish any given bayonet-locking relation or to disengage the same necessarily means that socket element 35 must be anchored against torsional displacement. To this end, diametrically opposite posts 45 extend parallel to each other from the flange for engagement with a selected pair of opposed openings 46, 46 in region B, and short outward lugs 48 at the ends of these posts secure an assembled relation of socket element 35 to region B. Such assembled relation may involve orientation of the major axis of flange 42 in the longitudinal direction of strip 36 when posts 45 are assembled to openings 46 (as is the case for the illustrations of FIGS. 6 and 7); alternatively, the major-axis orientation of flange 42 may be 90°-displaced, when posts 45 are assembled to openings 47, as is the case for the lower-leg positioning of socket 35 in FIG. 8. Generally, for a smaller-diameter limb region to be treated, it is desirable to employ the orientation shown in FIG. 8, wherein the minor-axis dimension of flange 42 presents minimum resistance to a uniform circumferential wrap of the afflicted limb.

In use, the bandage assembly described in connection with FIGS. 6 and 7 is first completed, preferably from a kit, comprising the components 35, 36, 37, so that option is available to the user for selection of socket-element orientation, as appropriate to the body region to be treated. Having completed the bandage assembly, a wrap of the afflicted body region is commenced, starting with region A, so positioned as to place the registered central openings of these components at the locale of desired ultrasonic-energy delivery. As the wrap progresses, VELCRO attachment progresses, to the point of completion when the separate finger strips of region D engage region B while straddling the central opening. The treatment head 12 is then applicable to the socket of element 35, after applying an excess of viscous acoustic gel to the front face of transducer 23, whereby upon insertion into the central opening in socket element 35, there can be assurance of a gel-filled volume in intimate acoustic-coupling relation with both the transducer face and the adjacent location of body tissue. In the course of such insertion, the orientation of the treatment head 12 will be understood to be at angular offset from the intended bayonet-locked orientation, so that the lugs or ridges 33, 34 can clear the locking lugs 44 of socket element 35. Upon achievement of a sufficient insertion, preferably involving slight compliant displacement of the transducer-mounting sleeve 22, a partial rotation of head 12 is operative to engage lugs 44 into one of the available sets of axial spaces between ridges 33, 34, whereby the intended orientation of head 12 becomes bayonet-locked and frictionally retained. Treatment can commence upon operation of switch 13, making sure that the green lamp is blinking at 26, thus signifying a correctly coupled acoustic delivery to the afflicted body region.

FIG. 9 shows a separate transducer head 50 for use in conjunction with electronics contained within the treatment head 12 of FIG. 1, for situations in which the treatment head 12 is too bulky to be practical for ambulation or for articulated movement of an afflicted limb. For example, an equine bone injury may be so close to the hoof as to preclude the kind of mounting described in connection with FIGS. 1 to 8.

The transducer head 50 of FIG. 9 is seen to comprise an elastomeric sylphon-bellows suspension 51 of a suitably coated thin transducer 52 with a flexible flaring lip 53 for better retention of coupling gel and for resilient adaptation to the local topography of the afflicted region; details of construction of transducer heads of sylphon-suspended variety are available from said co-pending application Ser. No. 628,403. At the other end of head 50, a rigid cup-shaped base 54 is the reference for the other end of bellows 51, and flexible electric cable 55 extends locally radially from and is sealed to the base 54. A jack fitting 56 will be understood to be compatible with the jack receptacle described at 31' in connection with FIGS. 4 and 5; when such jack connection is made, the arrangement internally of housing 14 is that ultrasonic-excitation energy and the monitoring of effectiveness of ultrasonic coupling to an afflicted region are transferred from the transducer 23 (of FIGS. 2 to 5) to the transducer 52 of FIG. 9.

In use, the base 54 of transducer head 50 is first seated within and against the rear flange 57 of the cup-shaped retainer 58 of FIG. 10, after first drawing cable 55 through the opening at flange 57 and locating the same within a side-entry slot 59 at the rear end and side wall of retainer 58. Thus assembled, the lip 53 and perhaps also the transducer 52 will be slightly cantilevered beyond the front end of retainer 50, where a mounting flange 60 extends outwardly; in this position, the bellows suspension 51 is unstressed but will be understood to have radial clearance with the bore 61 of retainer 58. The included volume of lip 53 is filled with acoustic-coupling gel and the loaded retainer 58 is applied directly to the afflicted region, with flange 60 against the limb or against a suitable pad which has been apertured to permit lip 53 to establish conforming contact with the limb. Bandaging material is wrapped around the afflicted region in such manner as at least to lap flange 60, holding the retainer and the transducer head in the desired location. Having thus secured the transducer head 50 for ultrasonic therapy of the desired region, the jack connection 31'/56 can be completed to a treatment head 12 which has been more conveniently mounted at another region of the same limb. Ultrasonic treatment and monitoring of transducer 52 and its coupling to the afflicted region will then proceed pursuant to switch 13 operation of the remotely mounted treatment head 12. Any excess cabling 55 between transducer head 50 and treatment head 12 can be simply taped to one or more intervening regions of the same limb.

In FIG. 11, a treatment head 12' is illustrated wherein a sylphon-mounted transducer 62 and lip 63 are united to a rigid tubular base 64 which is either integrally formed with a housing 14' of electronic components, as in the case of housing 14, or is flanged (as shown) for secure mounting to the front surface 15' of housing 14'. The peripheral dimensions of lip 63 and transducer 61 are sufficient for insertional entry into a bandage-mounted socket element 35 (FIGS. 6 and 7), to the extent permitting bayonet-locking engagement of socket lugs 44 in the axial space a' between opposing pairs of outward lugs 65 on the cylindrical body of base 64. Operation and use are as described in connection with FIGS. 1 to 8, with the greater flexibility of transducer (62) orientation which is available from an elastomeric sylphon-bellows suspension.

What is claimed is:

1. An orthopedic-treatment kit, comprising: a length of flexible bandage material sufficient between longitudinally spaced inner and outer wrapping ends to circumferentially wrap an injured body limb, with the outer end in overlap with the wrapped limb and with means to secure the wrap at the outer-end overlap; a pad of softly compressible material removably securable to said bandage at a location intermediate said ends, said pad having a central aperture and said bandage material having an aperture for registration with the aperture of said pad when in secured assembly thereto; a flanged annular socket element having a bore with radially inward bayonet-locking formations, said socket element being removably securable to said bandage aperture and with the flange interposed between said bandage material and said pad; and a transducer unit having a generally cylindrical mounting base and an axially projecting end, an ultrasonic transducer carried by said projecting end, said projecting end being sized for selective entry into and through the annulus of said socket element and through the aperture of said pad, and said base having formations for selective bayonet-locking engagement with the locking formations of said socket element upon predetermined passage of said transducer through the aperture of said pad.

2. The kit of claim 1, in which said pad and said bandage length and said socket element are preassembled to each other as a single one of the components of said kit.

3. The kit of claim 1, in which said socket element comprises an axially short cylindrical body with said flange extending radially outward of one axial end of said body.

4. The kit of claim 1, in which the bayonet-locking formations of said socket element are angularly spaced inward lug formations.

5. The kit of claim 4, in which the number of angularly spaced inward lug formations is four.

6. The kit of claim 1, in which said transducer is flat and mounted at said axially projecting end.

7. The kit of claim 1, in which the bayonet-locking formations of said mounting base are angularly spaced and are radially outward, and in which said socket element includes angularly spaced radially inward bayonet-locking lug formations corresponding to the bayonet-locking formations of said mounting base.

8. The kit of claim 7, in which the bayonet-locking formations of said mounting base are in like equal angularly spaced sets, the sets being at equal axial spacing whereby to accommodate bayonet-locked engagement with said socket element at different extents of passage through the annulus of said socket element.

9. The kit of claim 1, in which said transducer unit includes ultrasonic generator means connected for excitation of said transducer.

10. In combination, a socket element and an ultrasonic orthopedic-treatment head removably mounted to said socket element, for positioning said treatment head in orthopedic-treatment relation with an injured body limb, said socket element having a cylindrical annular body portion with a radially outward flange at one axial end and with a bore having a radially inward transducer-retaining formation at the opposite axial end, said orthopedic-treatment head comprising a generally cylindrical base adapted to be received in the bore of said body portion in axially located relation with said radially inward transducer-retaining formation, said treatment head further comprising a flat circular ultrasonic transducer and axially compressible elastomeric means positioning said transducer at such axial offset from said base as to apply said transducer with flexibly adapting and resiliently loaded contact with a body part to be treated, when the radially outward flange is mounted to or in close proximity to the body part.

11. A combination of claim 10, in which said radially inward transducer-retaining formation is a flange formation that is substantially circumferentially continuous.

12. The combination of claim 10, in which said radially inward formation is discontinuous at one angular location to define a slot for accommodating passage of an electrical lead to said treatment head when retained by said socket element.

13. The combination of claim 10, in which said radially inward transducer-retaining formation is a lug adapted for bayonet-locking retention of said generally cylindrical base.

14. The combination of claim 13, in which said lug is one of a plurality of angularly spaced lugs.

15. The combination of claim 14, in which said orthopedic-treatment head comprises at least one set of angularly spaced radially outward lug formations integrally formed with said base for selective bayonet-locking engagement with the lugs of said socket element.

16. The combination of claim 15, in which said set is one of a plurality of like axially spaced sets of radially outward lugs, whereby to afford axial selection of the bayonet-locked position of said head with respect to said socket element.

17. The combination of claim 16, wherein the axial space between adjacent sets is such that, upon bayonet-locking entry of said socket lugs in the space between adjacent sets, a slight interference-fit relation is encountered to frictionally retain the bayonet-locking engagement.

18. The combination of claim 13, in which said orthopedic-treatment head comprises at least one radially outward lug formation integrally formed with said base for selective bayonet-locking engagement with the lug of said socket element.

* * * * *